(12) United States Patent
Zhang

(10) Patent No.: US 8,215,163 B2
(45) Date of Patent: Jul. 10, 2012

(54) COATING RIGIDITY TESTING DEVICE

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 353 days.

(21) Appl. No.: 12/582,688

(22) Filed: Oct. 20, 2009

(65) Prior Publication Data

US 2011/0023593 A1   Feb. 3, 2011

(30) Foreign Application Priority Data

Aug. 3, 2009 (CN) .......................... 2009 1 0305122

(51) Int. Cl.
*G01N 19/04* (2006.01)
(52) U.S. Cl. .............................. 73/150 A; 73/7; 33/18.1
(58) Field of Classification Search ................ 73/150 A, 73/104, 105, 7, 1.81; 33/18.1, 19.2
See application file for complete search history.

(56) References Cited

U.S. PATENT DOCUMENTS 3,442,018 A * 5/1969 Viollet ............................ 33/832
6,826,840 B1 * 12/2004 Lindsey et al. ................ 33/18.1

* cited by examiner

*Primary Examiner* — Lisa Caputo
*Assistant Examiner* — Roger Hernandez-Prewitt
(74) *Attorney, Agent, or Firm* — Altis Law Group, Inc.

(57) ABSTRACT

A coating rigidity testing device includes a abrading machine, a base, two racks, and a actuator. The abrading machine is disposed on the base. The abrading machine includes a receiving chamber, a supporting arm, a pressure adjusting structure, and a scratching stylus. The receiving chamber includes a front plate. The extending arm includes a supporting arm is extended outwards from the front plate. The pressure adjusting member is extended outwards from the front plate and disposed above the supporting arm. The scratching stylus is received in the supporting arm, and configured for scratching nicks on a workpiece. The base includes a supporting surface supporting the abrading machine and the workpiece, and two first sidewalls parallel to each other. The two racks are arranged on two first sidewalls. The actuator is configured for driving the receiving chamber to move along the racks on the base.

10 Claims, 4 Drawing Sheets

COATING RIGIDITY TESTING DEVICE

BACKGROUND

1. Technical Field

The present disclosure relates to testing devices and, particularly, to a coating rigidity testing device.

2. Description of the Related Art

The coating rigidity of notebooks is directly related to the quality of notebooks' appearances. As a result, coating rigidity test is very important. However, the coating rigidity test is typically carried out manually. For example, a tester often manually scratch the workpiece by using a coin to determine whether the coating rigidity is up to requirement or not. However, since the pressure is uneven, the angle and speed of the coin-scratching cannot be precisely controlled, so that the test result is not accurate. Thereby, the manual testing procedures is time-consuming and inefficient.

Therefore, it is desirable to provide a coating rigidity testing device which can overcome the above-mentioned problems.

BRIEF DESCRIPTION OF THE DRAWINGS

Many aspects of the present coating rigidity testing device could be better understood with reference to the accompanying drawings. The components in the drawings are not necessarily drawn to scale, the emphasis instead being placed upon clearly illustrating the principles of the coating rigidity testing device. Moreover, in the drawings, like reference numerals designate corresponding parts throughout the several views.

DETAILED DESCRIPTION

Embodiments of the present coating rigidity testing device 10 will be now described in detail with reference to the drawings.

Figure 1:
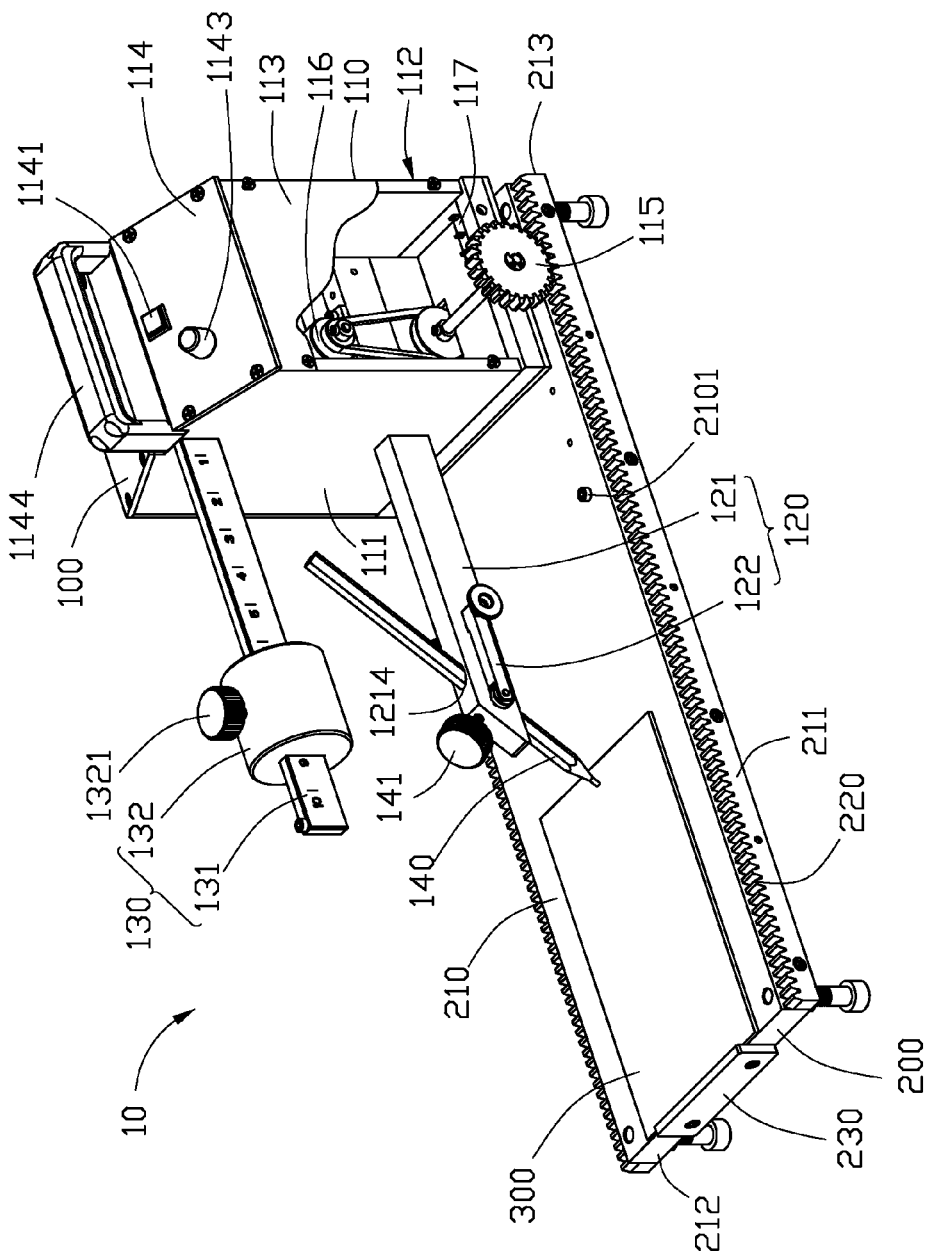
FIG. 1 is an assembled, isometric view of a coating rigidity testing device which includes a extending arm, according to an exemplary embodiment.
Figure 2:
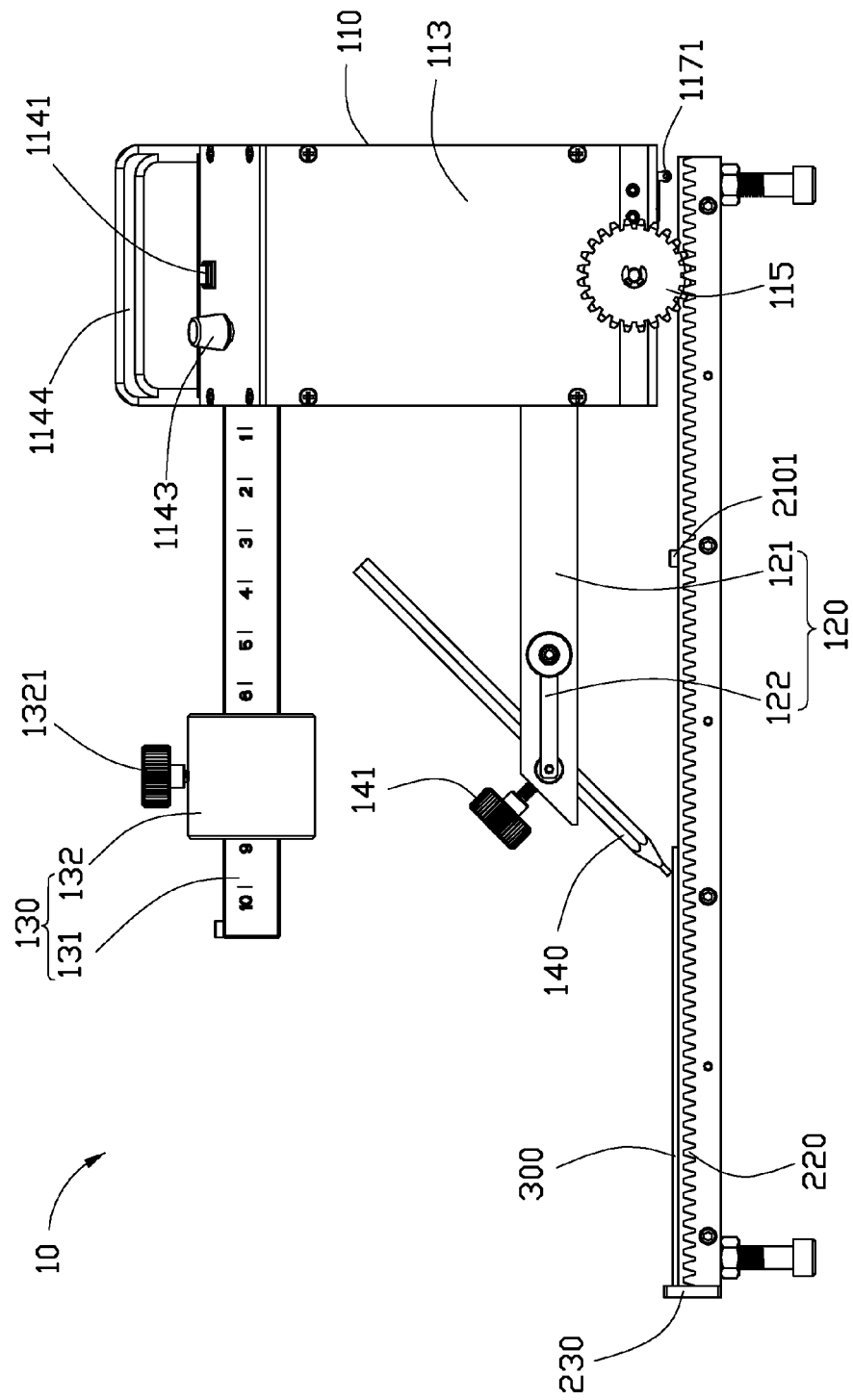
FIG. 2 is a side view of an exemplary embodiment of a coating rigidity testing device.

Referring to FIGS. 1-2, a testing device 10 according to an exemplary embodiment, is shown. The testing device 10 is configured for testing the costing rigidity of a workpiece 300. In this embodiment, the workpiece 300 is a cover/enclosure of a notebook. The coating rigidity testing device 10 includes an abrading machine 100 and a base 200. The base 200 is configured for supporting the workpiece 300 and the abrading machine 100. The abrading machine 100 is movable on the base 200.

The base 200 is rectangular in shape, and includes a supporting surface 210, two first sidewalls 211 parallel to each other, a second sidewall 212 substantially perpendicular to and connected to the two first sidewalls 211, and a third sidewall 213 substantially parallel to the second sidewall 212. The supporting surface 210 is configured for supporting the workpiece 300 and the abrading machine 100. A peg 2101 is mounted on the supporting surface 210. Two racks 220 are arranged on the two first sidewalls 211 of the base 200 correspondingly. A limiting wall 230 is positioned on the second sidewall 212. In this embodiment, the limiting wall 230 is configured for preventing the workpiece 300 from sliding out of the base 200.

The abrading machine 100 includes a receiving chamber 110, an extending arm 120, a pressure adjusting member 130, and an abrading scratching stylus 140.

The receiving chamber 110 is cuboid in shape and includes a front plate 111, a rear plate 112, two side plates 113, and an upper plate 114. The extending arm 120 and the pressure adjusting member 130 extend outwards substantially perpendicular from the front plate 111. In this embodiment, the pressure adjusting member 130 is disposed above the extending arm 120. An actuator 116 is disposed in the receiving chamber 110 and configured for driving two gears 115 meshed with the racks 220, respectively. The rotation of the gears 115 drives the receiving chamber 110 to move on the base 200. A switch 117 is positioned in the receiving chamber 110. The switch 117 includes a trigger end 1171 engageable with the peg 2101 when the receiving chamber 110 moves relative to the base 200 to a certain position. The switch 117 is actuated by the peg 2101 when the trigger end 1171 touches/engages the peg 2101. The switch 117 stops the receiving chamber 110 moving forward any further when triggered. A power knob 1141, a speed adjusting knob 1143, and a handle 1144 are positioned on the upper plate 114. The power knob 1141 is configured for supplying power and activating the actuator 116 when pressed, thus driving the receiving chamber 110 to move on the base 200. The speed adjusting knob 1143 is configured for adjusting a speed of the actuator 116, thus adjusting the speed of the receiving chamber 110 on the base 200. When the power knob 1141 is actuated, the actuator 116 is supplied with power until the switch 117 becomes actuated.

The pressure adjusting member 130 includes a gauge 131 and a weight 132. In this embodiment, the gauge 131 is parallel to the extending arm 120. The weight 132 is movably disposed on the gauge 131. The weight 132 can be secured to any position on the gauge 131 by a first securing screw 1321.

Figure 3:
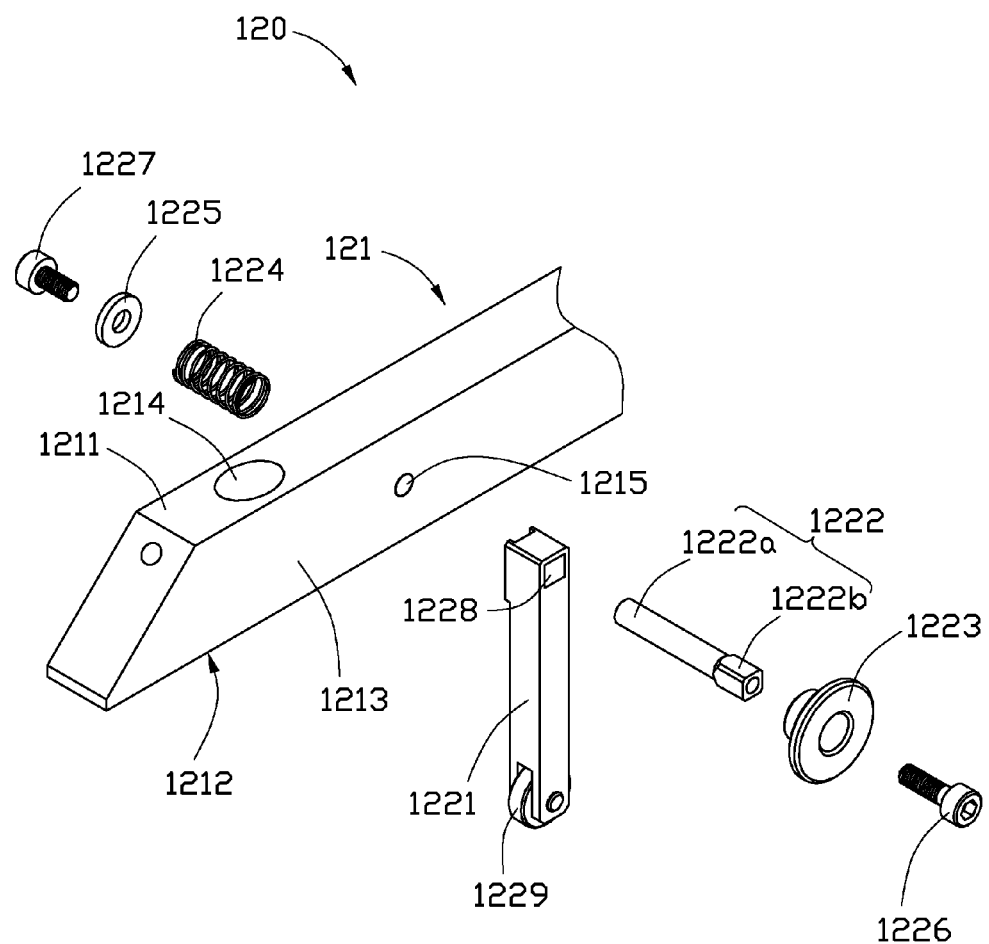
FIG. 3 is an exploded, isometric view of the extending arm of FIG. 1.
Figure 4:
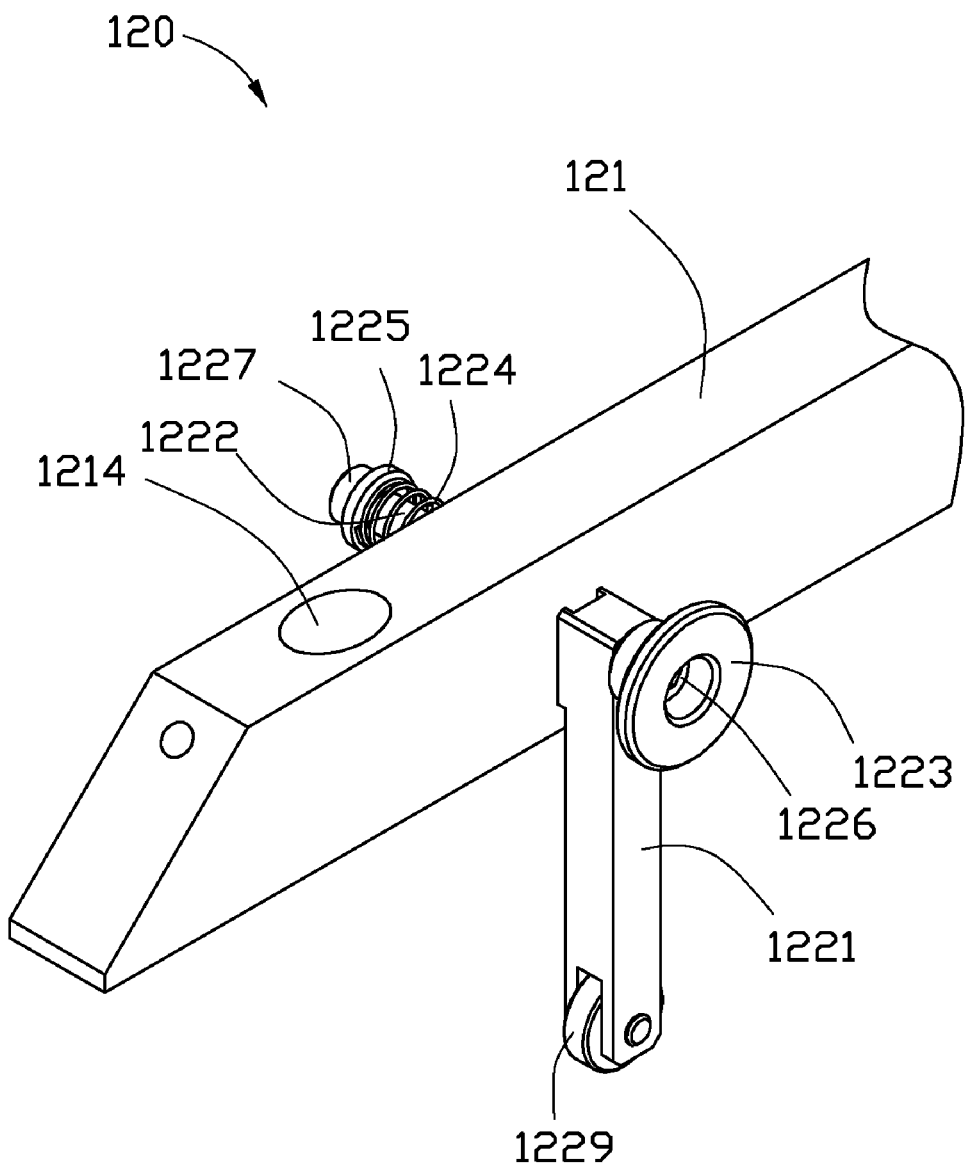
FIG. 4 is an assembled, isometric view of the extending arm of FIG. 3.

Also referring to FIGS. 3-4, the extending arm 120 includes a supporting arm 121 and a rotatable structure 122. The supporting arm 121 is substantially cuboid in shape, and extends outwards substantially perpendicular from the front plate 111. The supporting arm 121 includes a top surface 1211, a bottom surface 1212 opposite to the top surface 1211, and two sidewalls 1213. The supporting arm 121 defines a chute 1214 passing through the top surface 1211 and the bottom surface 1212. The chute 1214 is configured for receiving the scratching stylus 140. In this embodiment, the extending arm 120 also includes a second securing screw 141 for holding the scratching stylus 140 in the chute 1214. The supporting arm 121 also defines a circular through hole 1215 passing through the two sidewalls 1213 of the supporting arm 121.

The rotatable structure 122 is rotatably disposed on the supporting arm 121, and includes a supporting pole 1221, a guiding member 1222, a pull knob 1223, a spring 1224, a washer 1225, a first peg 1226, and a second peg 1227. A roller 1229 is positioned on one end of the supporting pole 1221, the other end of the supporting pole 1221 defines a square hole 1228. The guiding member 1222 includes a columnar portion 1222a and a rectangular portion 1222b formed on a distal end of the columnar portion 1222a. The rectangular portion 1222b matches with the circular through hole 1215 of the supporting arm 121. The diameter of the columnar portion 1222a is slightly smaller than the diameter of the circular through hole 1215. The first peg 1226 is inserted through the pull knob 1223 and is screwed into the rectangular portion 1222*b* of the guiding member 1222 to firmly attach the pull knob 1223 to the rectangular portion 1222*b* of the guiding member 1222. The rectangular portion 1222*b* is received in the square hole 1228. The columnar portion 1222*a* of the guiding member 1222 is inserted through the circular through hole 1215 and is sleeved in the spring 1224 and the washer 1225. The second peg 1227 is engaged into the columnar portion 1222*a*, and resists on the washer 1225.

In use, the workpiece 300 is disposed on the supporting surface 210 of the base 200, and resisted by the limiting wall 230. The scratching stylus 140 is inserted through the chute 1214 until the tip of the scratching stylus 140 touches the workpiece 300, the second securing screw 141 is adjusted to hold the position of the scratching stylus 140. The weight 132 on the gauge 131 is also adjusted to convert the weight of weight into pressure for the extending arm 121 via pressure converting means, so that the tip of the scratching stylus 140 exerts a desired pressure on the workpiece 300 to test the coating rigidity of the workpiece 300. After that, the rotation speed of the abrading machine 100 is selected by rotating the speed adjusting knob 1143. The power knob 1141 is pressed to power the abrading machine 100, thereby, the actuator 116 rotates the driving gear 115 to move the abrading machine 100 along the racks 220. As a result, the tip of the scratching stylus 140 slides against a surface of the workpiece 300 by the driving gear 115, etching an abrasion in the surface of the workpiece 300. The abrading machine 100 stops when the trigger end 1171 of the switch 117 is touched by the peg 2101 disposed on the supporting surface 210 of the base 200 and the power to the abrading machine 100 is accordingly cut off. A number of the abrasions can be etched on the workpiece 300 by raising the test machine 100 via the handle 1144 to change a position of testing machine 100 relative to the workpiece 300 and then actuating the actuator 116 to push the scratching stylus 140 forward on the surface of the workpiece 300.

After the scratching is finished, the rectangular portion 1222*b* of the guiding member 1222 is pulled out from the square hole 1228 of the supporting pole 1221 by pulling the pull knob 1223, so that the supporting pole 1221 rotates downwards about 90 degrees, the roller 1229 resists the supporting surface 210 of the base 200, the rectangular portion 1222*b* is then pushed into the square hole 1228 of the supporting arm 121 to restrict/prevent the supporting pole 1221 from rotating around the supporting arm 121. The supporting pole 1221 supports the supporting arm 121, thereby, preventing the tip of the scratching stylus 140 from being damaged. Finally, the depth of the nicks scratched by the abrading machine 100 is analyzed to determine whether the coating rigidity is satisfactory.

It will be understood that the above particular embodiments and methods are shown and described by way of illustration only. The principles and the features of the present invention may be employed in various and numerous embodiments thereof without departing from the scope of the invention as claimed. The above-described embodiments illustrate the scope of the invention but do not restrict the scope of the invention.

What is claimed is:

1. A coating rigidity testing device comprising:
    an abrading machine comprising:
        a receiving chamber comprising a front plate;
        an extending arm comprising a supporting arm extended outwards from the front plate;
        a pressure adjusting member extended outwards substantially perpendicular from the front plate; and
        an abrading scratching stylus supported by the supporting arm, and configured for scratching a workpiece being tested; and
    a base comprising:
        a supporting surface supporting the abrading machine and the workpiece;
        two first sidewalls parallel to each other;
        two racks arranged on the two first sidewalls;
        a second sidewall substantially perpendicular to and connected to the two first sidewalls, a limiting wall positioned on the second sidewall of the base, the limiting wall configured for preventing the workpiece from sliding out of the base; and
        an actuator disposed in the receiving chamber and configured for driving the abrading machine to move along the racks on the base.

2. The coating rigidity testing device as claimed in claim 1, wherein the receiving chamber further comprises a speed adjusting knob, the speed adjusting knob is configured for adjusting speed of the actuator to adjust the movement speed of the receiving chamber on the base.

3. The coating rigidity testing device as claimed in claim 1, wherein the supporting arm comprises a top surface, a bottom surface opposite to the top surface, and two sidewalls, the supporting arm defines a chute passing through the top surface and the bottom surface, the chute is configured for holding the scratching stylus.

4. The coating rigidity testing device as claimed in claim 3, wherein the extending arm also comprises a securing screw for locking the scratching stylus in the chute.

5. The coating rigidity testing device as claimed in claim 3, wherein the extending arm also comprises a rotatable structure rotatably disposed on the supporting arm, the rotatable structure is capable of rotating relative to the supporting arm, and is configured for preventing the tip of the scratching stylus from being damaged.

6. The coating rigidity testing device as claimed in claim 5, wherein the rotatable structure comprises a supporting pole, a guiding member, a pull knob, a spring, a washer, a first peg, and a second peg, one end of the supporting pole defines a square hole, the supporting arm also defines a circular through hole passing through the two sidewalls of the supporting arm, the guiding member comprises a columnar portion and a rectangular portion formed on a distal end of the columnar portion, the rectangular portion matches with the circular through hole, the first peg is inserted through the pull knob and is screwed into the rectangular portion to firmly attach the pull knob to the rectangular portion, the rectangular portion is received in the square hole, the columnar portion of the guiding member is inserted through the circular through hole and is sleeved in the spring and the washer, the second peg is engaged into the columnar portion and resists on the washer.

7. The coating rigidity testing device as claimed in claim 6, wherein a roller is positioned on the other end of the supporting pole.

8. The coating rigidity testing device as claimed in claim 6, wherein the diameter of the columnar portion is slightly smaller than the diameter of the circular through hole.

9. The coating rigidity testing device as claimed in claim 1, wherein a peg is mounted on the base, a switch is positioned in the receiving chamber, the switch comprises a trigger end engageable with the peg when the receiving chamber moves relative to the base, the switch is actuated by the peg when the trigger end touches/engages the peg, the switch stops the abrading machine moving forward any further when triggered.

10. The coating rigidity testing device as claimed in claim 1, wherein the pressure adjusting member comprises a weight and a gauge, the gauge is disposed above and parallel to the supporting arm, and the weight is movably disposed on the gauge, pressure adjusting member is configured for inserting pressure on the stylus via pressure converting means.

* * * * *